US007096868B2

(12) United States Patent
Tateo et al.

(10) Patent No.: US 7,096,868 B2
(45) Date of Patent: Aug. 29, 2006

(54) LARYNGEAL AIRWAY DEVICE

(75) Inventors: Lou Tateo, Discovery Bay, CA (US);
Hongha Le, Pleasant Hill, CA (US);
Douglas Clement, Livermore, CA (US);
Chun Hung Chen, Taipei (TW);
Muhua Huang, Taipei (TW)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 55 days.

(21) Appl. No.: 10/797,479

(22) Filed: Mar. 9, 2004

(65) Prior Publication Data

US 2005/0199244 A1    Sep. 15, 2005

(51) Int. Cl.
*A61M 16/00* (2006.01)
(52) U.S. Cl. ............................ 128/207.15; 128/207.14; 128/200.26
(58) Field of Classification Search ........... 128/207.15, 128/207.14, 200.26
See application file for complete search history.

(56) References Cited

U.S. PATENT DOCUMENTS

| | | | |
|---|---|---|---|
| 4,256,099 A | 3/1981 | Dryden | |
| 4,289,128 A | 9/1981 | Rüsch | |
| 4,509,514 A * | 4/1985 | Brain | 128/207.15 |
| 4,683,879 A | 8/1987 | Williams | |
| 4,995,338 A | 2/1991 | Brain | |
| 4,995,388 A | 2/1991 | Brain | |
| 5,241,956 A | 9/1993 | Brain | |
| 5,241,959 A | 9/1993 | Brain | |
| 5,249,571 A | 10/1993 | Brain | |
| 5,277,178 A | 1/1994 | Dingley | |
| 5,282,464 A | 2/1994 | Brain | |
| 5,297,547 A | 3/1994 | Brain | |
| 5,303,697 A | 4/1994 | Brain | |
| 5,305,743 A | 4/1994 | Brain | |
| 5,355,879 A | 10/1994 | Brain | |
| 5,391,248 A | 2/1995 | Brain | |
| 5,443,063 A | 8/1995 | Greenberg | |
| 5,477,851 A | 12/1995 | Callaghan et al. | |

(Continued)

FOREIGN PATENT DOCUMENTS

DE    10042172 A1    4/2001

(Continued)

OTHER PUBLICATIONS

Brimacombe, J. et al., "A comparison of the laryngeal mask airway ProSeal and the laryngeal tube airway in paralyzed anethetized adult patients undergoing pressure-controlled ventilation" Anesth Analg 95:770-6 (2002).

(Continued)

*Primary Examiner*—Henry Bennett
*Assistant Examiner*—Andrew Bunin
(74) *Attorney, Agent, or Firm*—Fletcher Yoder P.C.

(57) ABSTRACT

A laryngeal airway device, having an airway tube which has an internal passage in the airway tube wall for receiving a cuff inflation line, and a dome having an inlet and an outlet, where the dome is connected at its inlet with the distal end of the airway tube. The device also includes an annular spoon-shaped inflatable cuff connected with the periphery of the outlet of the dome; a cuff inflation line configured to be in fluid communication with the internal space of the cuff; and a multi-lobed aperture formed in the dome. The aperture is configured to be in fluid communication with the proximal end of the airway tube. The dome has protrusions forming the multi-lobed aperture, such that a flap is configured to prevent the obstruction of the aperture by a patient's epiglottis when the device is inserted into the patient.

43 Claims, 8 Drawing Sheets

U.S. PATENT DOCUMENTS

| | | | | |
|---|---|---|---|---|
| 5,513,627 A | * | 5/1996 | Flam | 128/207.15 |
| 5,584,290 A | * | 12/1996 | Brain | 128/207.15 |
| 5,623,921 A | | 4/1997 | Kinsinger et al. | |
| 5,632,271 A | | 5/1997 | Brain | |
| RE35,531 E | | 6/1997 | Callaghan et al. | |
| 5,653,229 A | | 8/1997 | Greenburg | |
| 5,682,880 A | | 11/1997 | Brain | |
| 5,711,293 A | | 1/1998 | Brain | |
| 5,743,258 A | | 4/1998 | Sato | |
| 5,746,202 A | | 5/1998 | Pagan | |
| 5,771,889 A | | 6/1998 | Pagan | |
| 5,791,341 A | * | 8/1998 | Bullard | 128/207.15 |
| 5,819,733 A | | 10/1998 | Bertram | |
| 5,850,832 A | * | 12/1998 | Chu | 128/200.26 |
| 5,853,004 A | | 12/1998 | Goodman | |
| 5,865,176 A | | 2/1999 | O'Neil | |
| 5,871,012 A | | 2/1999 | Neame et al. | |
| 5,878,745 A | * | 3/1999 | Brain | 128/207.15 |
| 5,881,726 A | | 3/1999 | Neame | |
| 5,896,858 A | * | 4/1999 | Brain | 128/207.15 |
| 5,937,860 A | | 8/1999 | Cook | |
| 5,979,445 A | * | 11/1999 | Neame et al. | 128/207.15 |
| 5,983,897 A | | 11/1999 | Pagan | |
| 5,988,167 A | | 11/1999 | Kamen | |
| 5,996,582 A | | 12/1999 | Turnbull | |
| 6,003,510 A | | 12/1999 | Anunta | |
| 6,003,514 A | * | 12/1999 | Pagan | 128/207.15 |
| 6,012,452 A | | 1/2000 | Pagan | |
| 6,021,779 A | | 2/2000 | Pagan | |
| 6,050,264 A | | 4/2000 | Greenfield | |
| 6,055,984 A | | 5/2000 | Brain | |
| 6,070,581 A | | 6/2000 | Augustine | |
| 6,079,409 A | | 6/2000 | Brain | |
| D429,811 S | | 8/2000 | Bermudez | |
| 6,095,144 A | | 8/2000 | Pagan | |
| 6,095,194 A | | 8/2000 | Pagan | |
| 6,116,243 A | | 9/2000 | Pagan | |
| 6,119,695 A | | 9/2000 | Augustine et al. | |
| 6,196,244 B1 | | 3/2001 | Alfery | |
| 6,240,922 B1 | * | 6/2001 | Pagan | 128/207.15 |
| 6,251,069 B1 | | 6/2001 | Mentzelopoulos et al. | |
| 6,257,236 B1 | | 7/2001 | Dutkiewicz | |
| 6,261,401 B1 | | 7/2001 | Pagan | |
| 6,266,548 B1 | | 7/2001 | Lamade et al. | |
| 6,308,703 B1 | | 10/2001 | Alving et al. | |
| 6,318,367 B1 | | 11/2001 | Mongeon | |
| 6,334,863 B1 | | 1/2002 | Srinivasan | |
| 6,338,343 B1 | | 1/2002 | Augustine et al. | |
| 6,386,199 B1 | | 5/2002 | Alfery | |
| 6,390,093 B1 | * | 5/2002 | Mongeon | 128/207.15 |
| 6,394,093 B1 | | 5/2002 | Lethi | |
| 6,422,239 B1 | | 7/2002 | Cook | |
| 6,427,686 B1 | | 8/2002 | Augustine et al. | |
| 6,439,232 B1 | * | 8/2002 | Brain | 128/207.15 |
| 6,533,761 B1 | | 3/2003 | Bertoch | |
| 6,546,931 B1 | | 4/2003 | Lin | |
| 6,604,525 B1 | | 8/2003 | Pagan | |
| 6,626,169 B1 | | 9/2003 | Gaitini | |
| 6,631,720 B1 | | 10/2003 | Brain | |
| 6,634,354 B1 | | 10/2003 | Christopher | |
| 6,668,832 B1 | | 12/2003 | Christopher | |
| 6,698,428 B1 | * | 3/2004 | Brain | 128/207.15 |
| 6,698,430 B1 | | 3/2004 | Van Landuyt | |
| 6,705,318 B1 | | 3/2004 | Brain | |
| 6,705,321 B1 | | 3/2004 | Cook | |
| 6,705,322 B1 | | 3/2004 | Chang | |
| 6,722,368 B1 | | 4/2004 | Shaikh | |
| 6,729,325 B1 | | 5/2004 | Alfrey | |
| 6,761,170 B1 | | 7/2004 | Van Landuyt | |
| 6,792,948 B1 | | 9/2004 | Brain | |
| 6,895,966 B1 | * | 5/2005 | Christopher | 128/207.15 |
| 2001/0015207 A1 | | 8/2001 | Pagan | |
| 2001/0025641 A1 | | 10/2001 | Doane et al. | |
| 2001/0032646 A1 | | 10/2001 | Christopher | |
| 2001/0039949 A1 | | 11/2001 | Loubser | |
| 2001/0050082 A1 | | 12/2001 | Kent | |
| 2002/138806 A1 | | 5/2002 | Brain | |
| 2002/0078961 A1 | | 6/2002 | Collins | |
| 2002/0095118 A1 | | 7/2002 | Bertoch et al. | |
| 2002/0112727 A1 | | 8/2002 | Van Landuyt | |
| 2002/0112728 A1 | | 8/2002 | Van Landuyt | |
| 2002/0170556 A1 | | 11/2002 | Gaitini | |
| 2003/0037790 A1 | | 2/2003 | Brain | |
| 2003/0051734 A1 | | 3/2003 | Brain | |
| 2003/0101998 A1 | | 6/2003 | Zocca et al. | |
| 2003/0192548 A1 | | 10/2003 | Chang | |
| 2004/0020491 A1 | | 2/2004 | Fortuna | |
| 2004/0060564 A1 | | 4/2004 | Brain | |
| 2004/0079364 A1 | | 4/2004 | Christopher | |
| 2004/0089307 A1 | | 5/2004 | Brain | |
| 2004/0112388 A1 | | 6/2004 | Russell | |
| 2004/0139971 A1 | | 7/2004 | Brain | |
| 2004/0200479 A1 | | 10/2004 | Chang | |
| 2004/0255953 A1 | | 12/2004 | Cook | |
| 2005/0005931 A1 | | 1/2005 | Doane et al. | |
| 2005/0016529 A1 | | 1/2005 | Cook | |
| 2005/0039756 A1 | | 2/2005 | Cook | |
| 2005/0051173 A1 | | 3/2005 | Brain | |
| 2005/0051175 A1 | | 3/2005 | Brain | |
| 2005/0066975 A1 | | 3/2005 | Brain | |
| 2005/0081861 A1 | | 4/2005 | Nasir | |
| 2005/0103345 A1 | | 5/2005 | Brain | |
| 2005/0274383 A1 | | 12/2005 | Brain | |

FOREIGN PATENT DOCUMENTS

| | | |
|---|---|---|
| DE | 10042172 A1 | 4/2001 |
| EP | 0842672 A2 | 5/1998 |
| EP | 0842672 A2 | 5/1998 |
| EP | 0857492 A2 | 8/1998 |
| EP | 0857492 A2 | 8/1998 |
| EP | 0865798 A2 | 9/1998 |
| EP | 0865798 A2 | 9/1998 |
| FR | 2843306 A1 | 2/2004 |
| FR | 2843306 A1 | 2/2004 |

OTHER PUBLICATIONS

Mason, A., "Method of securing the laryngeal mask airway in pre-hospital care" Pre-hospital Immediate Care 3:167-169 (1999).

Miller, H., "Laryngeal mask airway—an update" Denver Health Medical Center/University of Colorado Health Sciences Center, pp. 1-10, (undated).

Pinosky, M., "Laryngeal mask airway: uses in anesthesiology" pp. 1-5, retrieved online from <http://www.sma.org/smj/96jun1.htm> on Aug. 8, 2003.

Goudsouzian, Nishan G., et al.; "Radiologic Localization of the Laryngeal Mask Airway in Children," *Anaethesiology*, vol. 77, (1992) pp. 1085-1089.

Shorten, George D., "Airway management," *Anaesthesiology*, vol. 5, pp. 772-775 (1992).

Roberts, James T. et al.; "Using the Bubble Inclinometer to Measure Laryngeal Tilt and Predict Difficulty of Laryngoscopy," *J. Clin. Anesth.*, vol. 5, Jul./Aug. 1993, pp. 306-309.

Roberts, James T., et al.; "Using the Laryngeal Indices Caliper to Predict Difficulty of Laryngoscopy with a Macintosh #3 Laryngoscope," *J. Clin. Anesth.*, vol. 5, Jul./Aug. 1993, pp. 302-305.

Shorten, George D., et al.; "Chapter 20: The Laryngeal Mask and Perioperative Airway Management,", *Clinical Management of the Airway*, pp. 219-227 (1994).

Roberts, James T., "Clinical Management of the Airway," W.B. Saunders Company, 1994 (Table of Contents only).

Shorten, G.D., et al.; "Assessment of Upper Airway Anatomy in Awake, Sedated and Anaesthetised Patients Using Magnetic Resonance Imaging," *Anaesth. Intens Care*, vol. 22, (1994), pp. 165-169.
Ruby, Ralph R. F., et al.; "Laryngeal Mask Airway in Paediatric Otolaryngologic Surgery," *The Journal of Otolaryngology*, vol. 24, No. 5, pp. 288-291 (1995).
Shorten, G.D., et al.; "Assessment of the effect of head and neck position on upper airway anatomy in sedated paediatric patients using Magnetic Resonance Imaging," *Paediatric Anaesthesia*, vol. 5, pp. 243-248 (1995).
Shorten, George D., et al.; "Assessment of Patient Position for Fiberoptic Intubation Using Vidolaryngoscopy," *Journal of Clinical Anesthesia*, vol. 7, pp. 31-34 (1995).
UCSD Anesthesiology Laryngeal Mask Airways, "Drawer Two: Laryngeal mask airways, suction catheters, Yankauer tip", by J. Clark Venable, M.D., http://anes-som.ucsd.edu/Airway/Drawer2/DR2lma.html, last updated Oct. 1, 1996 (23 pgs.).
Verghese, Chandi, et al.; "Survey of Laryngeal Mask Airway Usage in 11,910 Patients: Safety and Efficacy for Conventional and Nonconventional Usage," *Anesth Analg*, vol. 82, pp. 129-133, 1996.
Brimacome, J.R., et al.; "The Laryngeal Mask Airway—A Review and Practical Guide," W. B. Saunders Company, Ltd., 1997.
Baskett, P.J.F., et al.; " APPARATUS: The intubing laryngeal mask—Results of a multicentre trial with experience of 500 cases," *Anaethesia*, vol. 53, pp. 1174-1179 (1998).
Mason, A., "Method of securing the laryngeal mask airway in pre-hospital care" Pre-hospital Immedicate Care 3:167-169 (1999).
Rosenblatt, William H., et al.; "The Intubating Laryngeal Mask: Use of a New Ventilating-Intubating Device in the Emergency Department," *Anals of Emergency Medicine*, vol. 33, No. 2, February 1999, pp. 234-238.
LMA-ProSeal™ User Guide, LMA North America, Inc., 2 pages (2001).
Ferson, David Z., et al.; "Use of the Intubating LMA-Fastrach™ in 254 Patients With Difficult-to-manage Airways," *Anesthesiology*, vol. 95, No. 5 Nov. 2001, pp. 1175-1181.
Roberts, James T., et al.; "Chapter 18; The Prediction of Difficult Intubation," Harvard Electronic Anesthesia Library, Lippincott Williams and Wilkins, pp. 183-186 (2001).
Ahmed, M. Zubair, et al.; "The reinforced laryngeal mask airway (RLMA) protects the airway in patients undergoing nasal surgery—an observational study of 200 patients," *Cardiothoracic Anesthesia, Respiration and Airway;* vol. 49, No. 8, Jan. 2002, pp. 863-866.
Maltby, J. Roger, et al.; "The LMA-ProSeal™ is an effective alternative to tracheal intubation for parascopic cholecystectomy;" *Cardiothoracic Anesthesia, Respiration and Airway*, vol. 49, No. 8, Jan. 2002, pp. 857-862.
Maltby, J. Roger, et al.; "LMA-Classic™ and IMA-ProSeal™ are effective alternatives to endotracheal intubation for gynecologic laparoscopy," *Cardiothoracic Anesthesia, Respiration and Airway*, vol. 50, No. 1; Jun. 2002, pp. 71-77.
O' Connor Jr., et al., "Assessing ProSeal Laryngeal Mask Positioning: The Superasternal Notch Test," *Anesthesia & Analgesia*, vol. 94, No. 5, May 2002, Letters to the Editor p. 1.
Brimacombe, J. et al., "A comparison of the laryngeal mask airway ProSeal and the laryngeal tube airway in paralyzed anesthetized adult patients undergoing pressure-controlled ventilation" *Anesth Analg* 95:770-6 (2002).
Genzwuerker, Harald V, et al., "Comparing Laryngeal Mask Airway ProSeal and Laryngeal Tube", Anesth Analg. (2003) 96:1535-1536.
LMA Flexible™ Brochure, LMA North America, Inc. 2 pages (2003).
LMA Unique™ Unique, LMA North America, Inc., 2 pages (2003).

King Systems Corporation, "Completing the Algorithm . . . The KING LT™ Oropharyngeal Airway", 6 pages, Jan. 2003.
Samarkandi, A. et al.; "The role of laryngeal mask airway in cardiopulmonary resuscitation,"; http://www.angelfire.com/mt/CPR/Art10.html, printed from website Aug. 8, 2003 (4 pgs.).
Pinosky, M., "Laryngeal mask airway: uses in anesthesiology" pp. 1-5, retrieved online from <http://www.sma/org/smj/96jun1.htm> on Aug. 8, 2003.
Goody, Norman L., "Using the Laryngeal Mask Airway", Walter Reed Army Medical Center, Surgery Department , Anesthesia Articles, www.wramc.amedd.army.mil/departments/surgery/Anesthesiology/lma.ppt, printed from website Aug. 14, 2003.
LMA North America Inc. Product Listing and Brochures for LMA ProSeal™, LMA Unique™, LMA Classic™, LMA Flexible™and LMA Fastrach™ ; http://www.lmana.com/prod/comonents/products/products.html, printed from website Aug. 14, 2003 and Dec. 5, 2003.
LMA North America, Inc., History and Development of the LMA™ Airway, http://www.lmana.com/prod/components/history_development.html, printed from website Aug. 14, 2003 (2 pgs.).
LMA North America, Inc., Dr. A.I.J. Brain—LMA™ Airway Inventor, http://www.lmana.com/prod/components/brain_bio.html , printed from website Aug. 14, 2003 (2 pgs.).
LMA Safe Guard, Customer Questions, http://www.intaventorthofix.com/safeguard_4.html , printed from website Aug. 14, 2003 (4 pgs.).
Osborn, Irene, "The Airway Carnival: Laryngeal Mask Airway", http://www.airwaycarnival.com, printed from website Aug. 14, 2003 (2 pgs.).
Laryngeal mask airway, General Practice Notbook, http://www.gpnotebook.co.uk/cache/-2006253523.htm , printed from website Dec. 15, 2003 (1 pg.).
Still Not So Hot On Research, Business World-Cover Story, http://www.businessworldinidia.com/archive/200410/cover2.htm, printed from website Dec. 5, 2003 (2 pgs.).
Akça, Ozan, et al.; "Clinical Comparison Between a New Perilaryngeal Airway (PLA™ ) and the Laryngeal Mask Airway (LMA®)"; 2 pages undated.
CobraPLA™ Single use Perilaryngeal Airway Brochure, Engineered Medical Systems, Inc., 2 pages undated.
CobraPLA™ Advantages Brochure, 1 page undated.
Revised LMA Program—"Pre-Hospital Laryngeal Mask Airway Insertion Program Overview", Commonwealth of Massachuetts, Dept. of Public Health, Office of Emergency Medical Services, EMT Index (7 pgs.) undated.
LMA ProSeal™ Brochure, LMA North America, Inc., 2 pages undated.
Miller, H., "L aryngeal mask airway—an update" Denver Health Medical Center/University of Colorado Health Sciences center, pp. 1-10, undated.
VBM Laryngeal Tube LTS Brochure, 2 pages undated.
VBM Laryngeal Tube LT® , 2 pages undated.
Shorten, G. D., "Prediction of Difficult Intubation," Harvard Electronic Anesthesia Library, Lippincott Williams and Wilkins, pp. 183-186 (2001).
ASTM F29.12.07 Subcommittee—Anesthetic and respirtoray equipment—Standard Specification for supralaryngeal airways and connectors (Jul. 8, 2003).
Brimacome, Joseph R., "Second Edition—Laryngeal Mask Anesthesia, principles and practice" Saunders, (2005).

* cited by examiner

Section A-A

Section A-A

LARYNGEAL AIRWAY DEVICE

BACKGROUND OF THE INVENTION

The present invention relates to laryngeal airway devices. More specifically, the present invention relates to improved geometric and design configurations for laryngeal airway devices.

It is common practice to use an airway device known as a laryngeal mask for the administration of anesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are provided by many suppliers.

The laryngeal airway is a device that fills the gap between tracheal intubation and the use of a face mask. The laryngeal airway device is inserted blindly into the pharynx and forms a low pressure seal around the laryngeal inlet. It is minimally stimulating to the airway, thus avoiding the unwanted sympathetic stimulation associated with laryngoscopy. The laryngeal airway device provides a way of establishing an airway during anesthesia in both adults and children, and plays a useful role in management of the difficult airway.

As show in FIG. 1, a common laryngeal airway device is constructed of medical-grade silicone rubber with no latex in any part. This allows the laryngeal airway device to withstand repeated autoclaving. The device has a shaft or airway tube 1 ranging from 5.25 to 12 mm in internal diameter, depending on the size of the laryngeal airway device. The shaft is fused at an angle to a distal elliptical spoon-shaped mask 2 with an inflatable rim or cuff resembling a miniature face mask. The shaft opens into the concavity of the ellipse via an aperture having aperture bars 3 across the opening to prevent the epiglottis from falling back and blocking the lumen. Various different size laryngeal airway devices are available to accommodate different size patients, from neonates to adult patients.

When correctly positioned, the tip of the laryngeal airway device cuff lies at the base of the hypopharynx against the upper esophageal sphincter, the sides lie in the pyriform fossae, and the upper border of the mask lies at the base of the tongue, pushing it forward. The epiglottis often lies within the bowl of the laryngeal airway device, but the device functions satisfactorily with the epiglottis in the upright horizontal or downfolded position. When the cuff is around the opening to the larynx, a syringe connects to the valve 4 to inject air into the cuff via the inflation line 5 to inflate the cuff, such that no gap is present between the cuff and the larynx. The inflation line 5 meets the cuff 2 at an inflation line inlet 8, which inlet 8 is typically also the mold extraction point or orifice used during the forming of the cuff 2. An inflation line balloon 6 reflects the degree of inflation of the cuff. Typically, the airway tube includes a securely attached 15 mm connector 7 at its proximal end.

However existing laryngeal airway devices suffer from various shortcomings. For example, the aperture bars across the airway opening prevent the entry of other devices, such as bronchoscopes and/or endotracheal tubes into the airway passage. The spoon-shaped cuff is inflated at its proximal end by a separate inflation line. In some devices, the inflation line inlet at the proximal end of the cuff is also the same as the mold extraction orifice used to form the cuff, and protrudes away from the surface of the cuff, resulting in a nonsmooth external surface for the cuff. The separate inflation line needs to be carefully handled as the laryngeal airway device is inserted into a patient's airway. It has been reported by many that the cuff folds back on itself as the laryngeal airway device is being inserted. The folded cuff prevents the cuff from being properly inflated thus preventing effective placement of the device. In addition, the commonly placed 15 mm connector at the proximal end of the airway tube can also prevent the insertion of other devices into the airway tube.

There is therefore a need for an improved laryngeal airway device that does not suffer from these shortcomings.

SUMMARY

Certain aspects commensurate in scope with the disclosed embodiments are set forth below. It should be understood that these aspects are presented merely to provide the reader with a brief summary of certain forms the invention might take and these aspects are not intended to limit the scope of the invention. Indeed, the invention may encompass a variety of aspects that may not be set forth below.

The present invention is directed to a laryngeal airway device. In one embodiment, the present invention provides a laryngeal airway device having an airway tube which has an internal passage in the airway tube wall for receiving a cuff inflation line. The device also has a dome having an inlet and an outlet, which is connected at its inlet with the distal end of the airway tube; an annular spoon-shaped inflatable cuff connected with the periphery of the outlet of the dome; a cuff inflation line configured to be in fluid communication with the internal space of the cuff; and a multi-lobed aperture formed in the dome. The aperture is configured to be in fluid communication with the proximal end of the airway tube. The dome also has several protrusions forming the multi-lobed aperture, such that a flap is configured to prevent the obstruction of the aperture by a patient's epiglottis when the device is inserted into the patient.

In one aspect, the device also includes a protruding dome tip connected with the distal end of the outlet of the dome. The protruding dome tip's distal end is located in and in fluid communication with the internal space of the cuff.

In another aspect, the dome also includes a groove that is configured to hold the cuff inflation line in the dome.

In another aspect, the outlet of the dome further includes a tray portion, and the cuff further includes a channel on the inner surface of the annular shaped cuff, such that the channel is connected with the periphery of the outlet of the dome at the tray portion.

In another aspect, the cuffs outer surface is formed in the absence of external protrusions. The cuff also includes a mold extraction orifice at its distal end, which is formed on an internal surface of the cuff, and wherein the cuff inflation line is configured to be in fluid communication with the internal space of the cuff at an opening which includes the mold extraction orifice.

In another aspect, the device also includes a removable connector connected with the proximal end of the airway tube.

In another aspect, the cuff inflation line is configured to be in fluid communication with the internal space of the cuff at a distal end of the cuff. The device also includes an inflation line insertion point offset distally from the proximal end of the airway tube, where the insertion point serves as the proximal end and is integral with the internal passage.

For a further understanding of the nature and advantages of the invention, reference should be made to the following description taken in conjunction with the accompanying drawings.

DETAILED INVENTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 2:
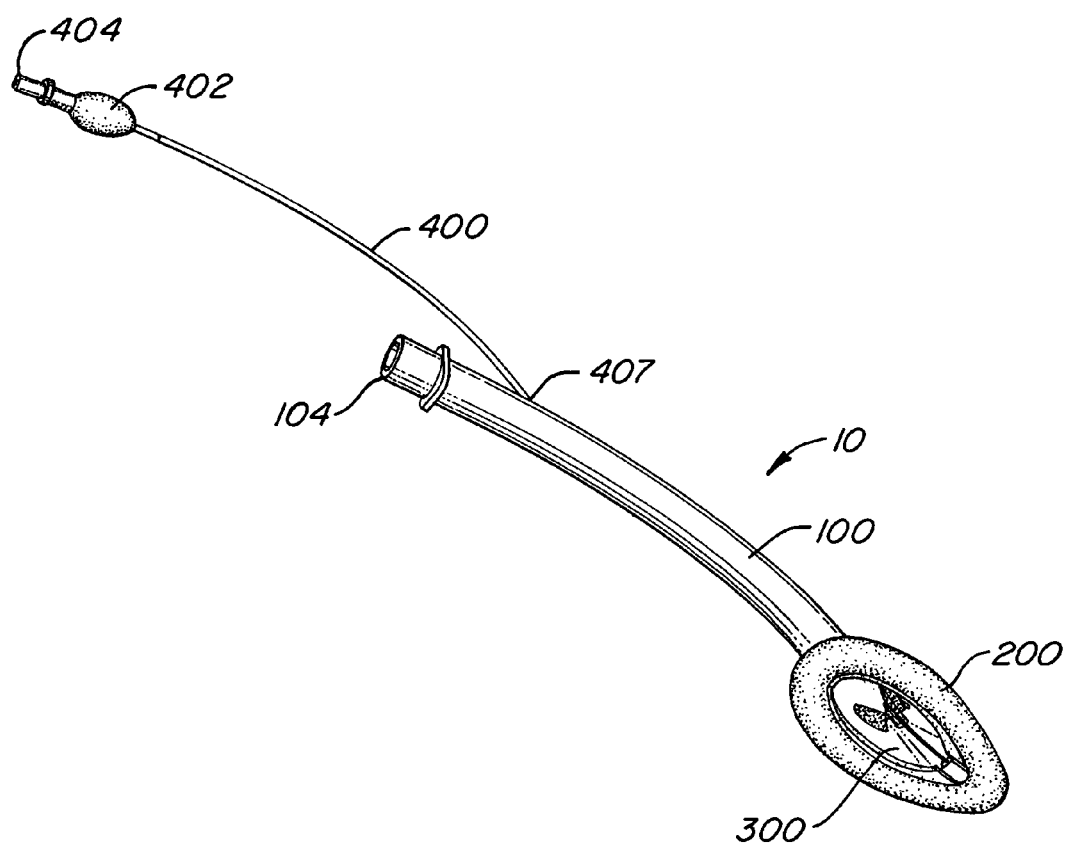
FIG. 2 is a perspective view diagram of a laryngeal airway device in accordance with an embodiment of the present invention.

FIG. 2 is a perspective view diagram of a laryngeal airway device 10 in accordance with an embodiment of the present invention. An airway tube 100 connects at the tube's distal end with a dome 300. At its proximal end the tube 100 is connected with a removable connector 104. In contrast to the more common way of adhesively attaching the connector with the tube, the connector 104 is press fitted into place and not adhesively adhered with the tube 100. In this manner, the connector 104 is easily removable to allow the insertion of another device, such as for example an endotracheal tube or bronchoscope through the airway tube 100. An endotracheal intubation introduces a tube into the trachea to provide an open airway to administer oxygen, gaseous medication, or anesthetics; it may also be done to remove blockages, or to view the interior walls. Therefore, by enabling the removal of the connector 104, the in-place laryngeal airway device can also facilitate an endotracheal intubation. A cuff 200 connects with the dome 300. The dome 300 has a multi-lobe shaped aperture and is described in further detail below. An inflation line 400 enters the tube 100 at the inflation line insertion location 407 and feeds through the tube 100. The inflation line 400 continues through the tube 100, runs through a groove in the dome 300, and connects with the cuff at the distal end of the cuff. The cuff 200 has a smooth external surface that is void of any protrusions. A syringe is used to connect with the valve 404 to fill the cuff with air to inflate it. The valve 404 is a check valve and prevents the passive backflow of air from the cuff. An inflation balloon 402 connected downstream of the valve 404 provides an indication of the inflation level of the cuff. The inflation line insertion location 407 is offset back from the proximal end of the tube 100 to enable the operation of the device even when there is a need to cut off the proximal end. The offset of the inflation line insertion location 407 from the proximal end of the tube 100 allows for a significant portion of the tube 100 to be cut off and still not adversely impact the inflation or deflation operation of the cuff.

Figure 3:
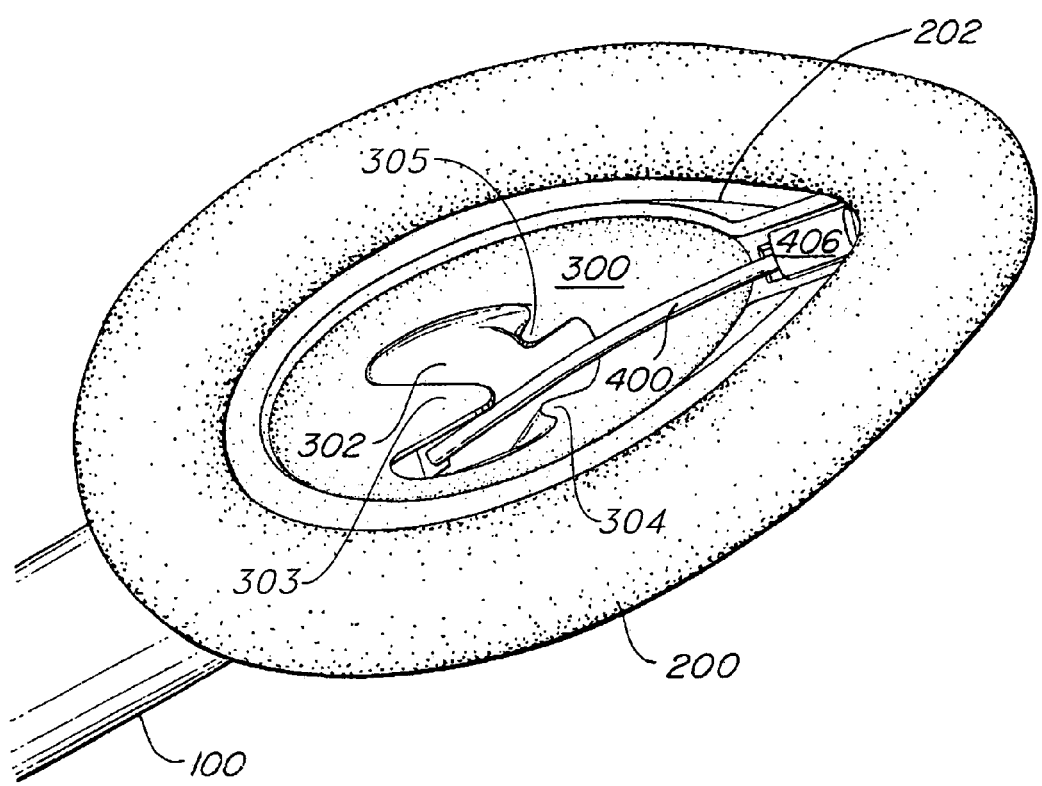
FIG. 3 is a detailed view diagram of the bottom or airway side of the distal end of the device of FIG. 2.

FIG. 3 is a detailed view diagram of the bottom or airway side of the distal end of the device of FIG. 2. FIG. 3 shows the tube 100 ending at the dome 300. The dome has an aperture or opening 302 and a groove along its upper portion. The groove is configured to receive the inflation line 400. The inflation line 400 travels along the groove and meets connector 406, which is used to deliver air to inflate the cuff 200. The aperture has multiple lobes, preferably elongated. Defining the lobes are protrusions 303, 304, and 305 which separate them. One of the protrusions 303 is formed at the proximal end. This protrusion 303 comprises a flexible flap, preferably tongue-shaped, and larger than the other protrusions 304 and 305. The smaller protrusions 304 and 305 are preferably less flexible, or more rigid than the flap 303. The aperture 302 is shaped in this manner to help prevent the epiglottis's obstruction of the airway. In addition, the protrusions 303, 304 and 305 of the multi-lobed design (as opposed to the more common bars that fully extend across such an opening) allow the entry of other devices, (e.g., a bronchoscope or an endotracheal tube) into the airway passage. When such other devices are being entered into the airway passage, the flap bends 303 and pushes the epiglottis back enabling the effective insertion of the bronchoscope or other device into the airway. None of the protrusions 303, 304, and 305 extend fully across the airway opening. The protrusions 303, 304, and 305 may be integrally molded with the dome.

The cuff 200 is attached with the dome using known techniques. In addition, the cuff includes a channel 202 on its inner surface that is configured to couple with a complimentarily shaped tray 412 (shown in FIG. 4) on the lower side of the dome. The channel 202 and tray 412 together provide for an improved bonding surface that provides a more secure structure for adhering the cuff with the dome. The channel and tray arrangement also ensure a proper mechanical fit by enabling a centered fit between the spoon-shaped cuff and dome. The channel and tray arrangement also enable a more repeatable assembly of the cuff with the dome.

Figure 4:
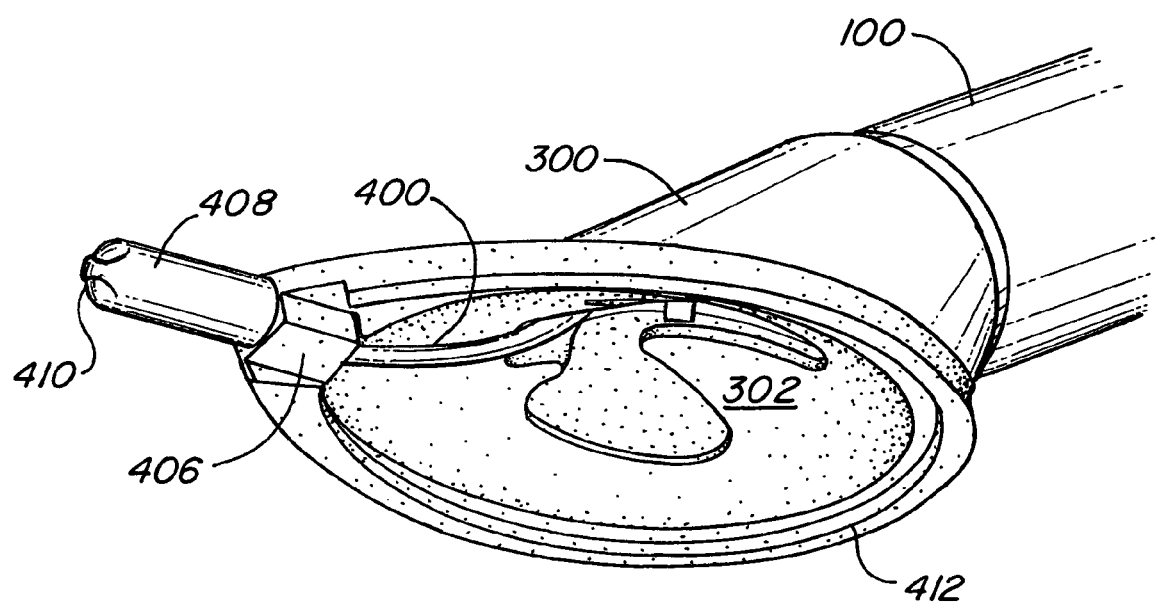
FIG. 4 is a detailed view diagram of FIG. 3 shown without the cuff.
Figure 5:
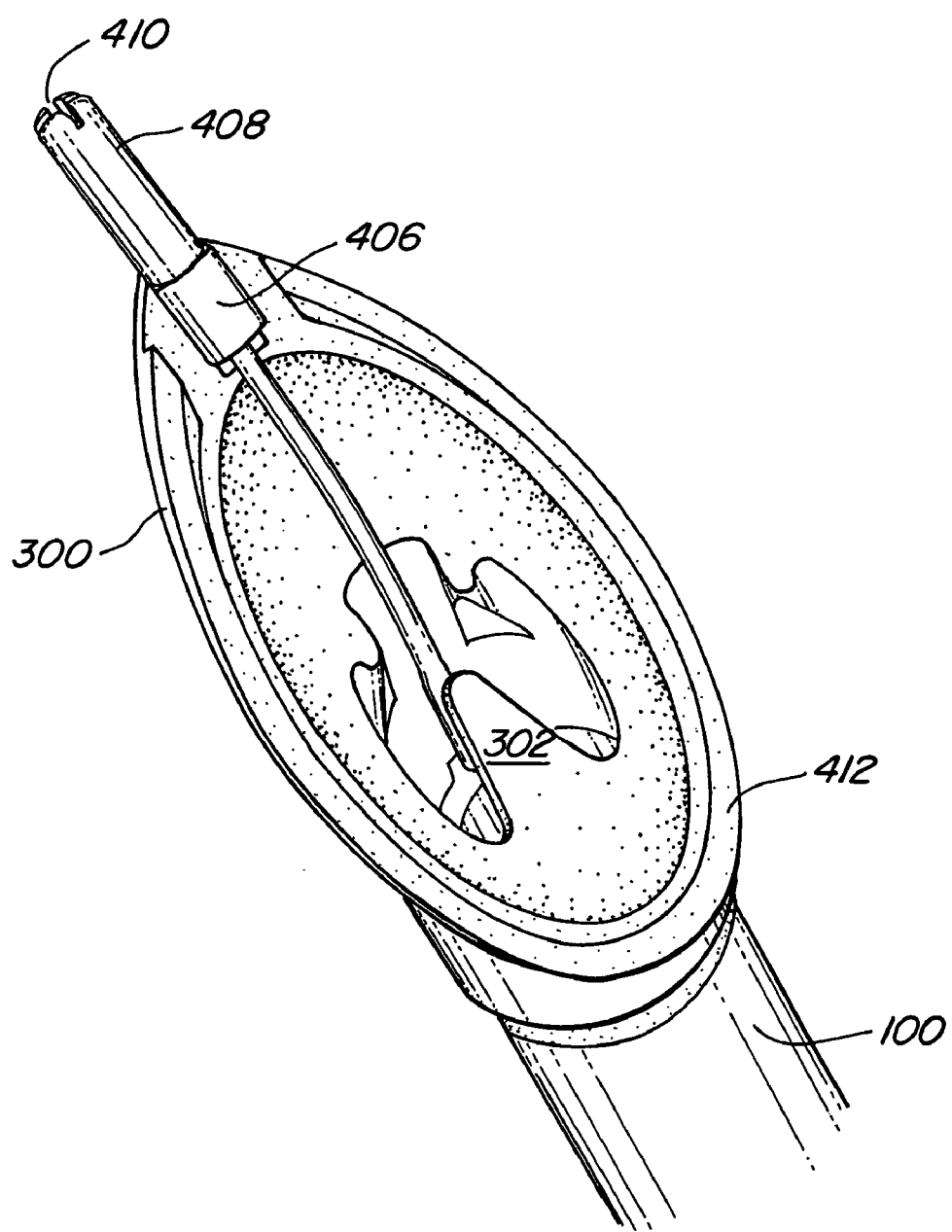
FIG. 5 is another perspective view of the device of FIG. 4.

FIG. 4 is a detailed view diagram of FIG. 3 shown without the cuff 200. As set forth above, FIG. 4 shows the tube 100 ending at the dome 300. Surrounding the dome, at least partially, is tray 412. The channel 202 (shown in FIG. 3) and tray 412 together provide an improved bonding surface that provides a more secure structure for adhering the cuff with the dome. The tray 412 may be integrally formed with the dome 300, or it may be a separate piece that is adhered to or bonded with the dome 300. The dome 300 has a multi-lobed aperture 302 and a groove along its upper portion. The groove is configured to receive the inflation line 400. The inflation line 400 meets connector 406, which is used to deliver air to inflate the cuff 200. The multi-lobed aperture 302 is shaped in this manner to help prevent the epiglottis's obstruction of the airway. Also shown is a protruding dome tip 408 connected with and extending from the connector 406. The protruding dome tip 408 fits inside the cuff at the cuff's distal end to help prevent the cuff from folding back during insertion. In one embodiment, the protruding dome tip 408 is less elastic than the cuff, to help prevent the cuff from folding back on itself when the device is being inserted into a patient. In one embodiment, the protruding dome tip 408 has a cross cut structure or side slits 410 at its distal end to help prevent possible air-occlusion, especially during the removal of the laryngeal airway device that could be caused by the adjacent placement of the cuff's interior wall against the distal end of the dome tip 408. Other slit or cut forms can be envisioned that enable the flow of air between the cuff and the air inflation line, even when the cuff's internal surface is held against the dome tip. Such cut forms include a slot, a Philips type slot, a star form and so on. FIG. 5 is another perspective view of the device of FIG. 4.

Figure 1:
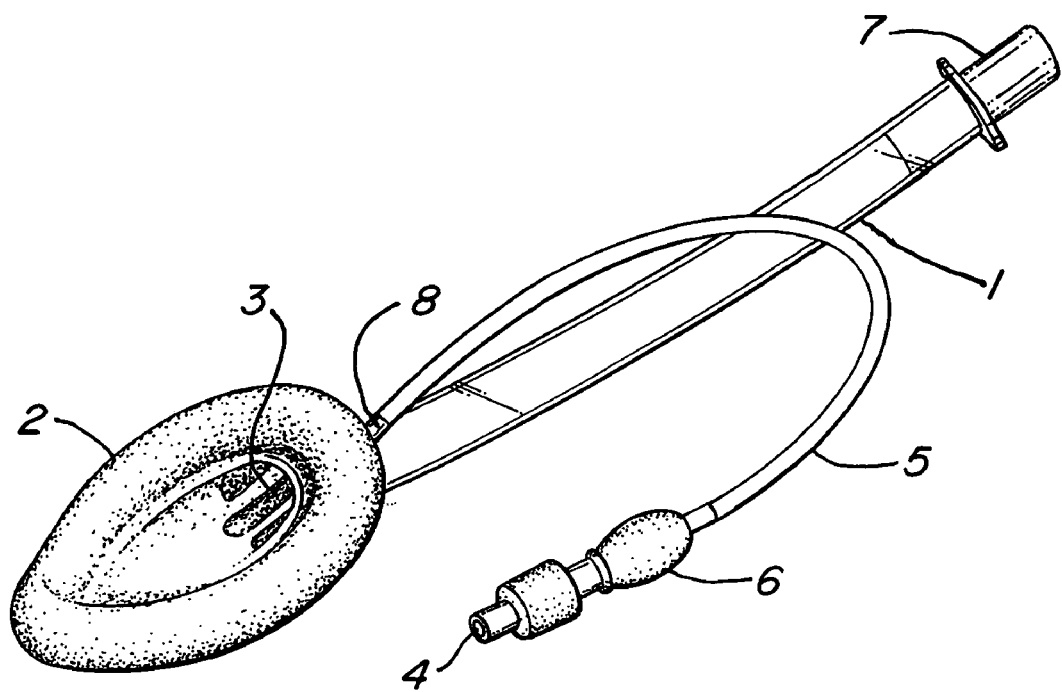
FIG. 1 is a diagram of a prior art laryngeal airway device.
Figure 6:
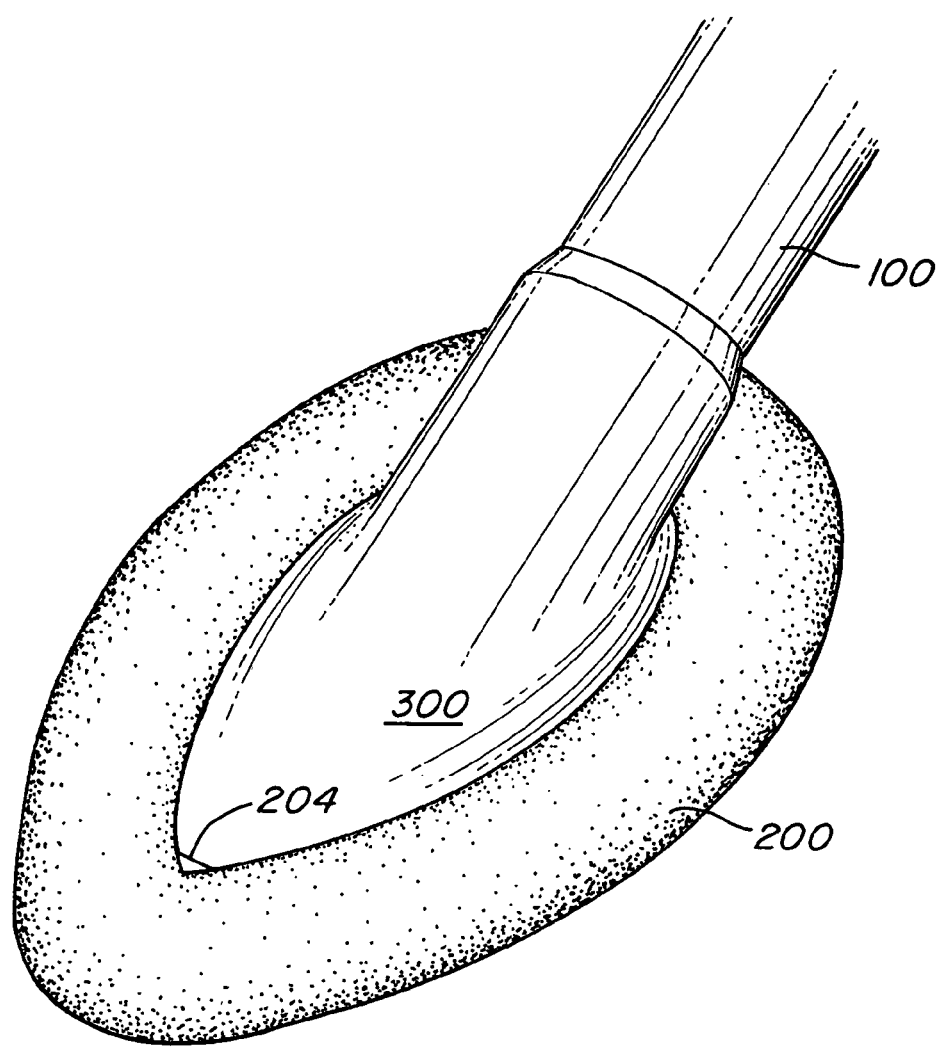
FIG. 6 is a top view diagram of the device of FIG. 3.

FIG. 6 is a top view diagram of the device of FIG. 3. FIG. 6 shows the tube 100 ending at its distal end at the dome 300. The dome 300 is encircled by the complimentarily and spoon-shaped cuff 200. The cuff 200 has a smooth external surface to help prevent trauma that could be caused by externally protruding projections from the cuff's external surface, in contrast to common prior art devices (e.g., see FIG. 1). Mold extraction orifice 204 is located at the distal internal end (instead of proximal external end, e.g., as shown in FIG. 1) of the cuff 200 and is at the same location as that of the dome insertion to ensure a smooth external cuff surface. Moreover, having the mold extraction orifice 204 located at the same location as that of the dome insertion, ensures a simplified manufacturing process for the laryngeal airway device in accordance with the embodiments of the present invention, and thus will increase production throughput and reduce the cost of each unit.

Figure 7:
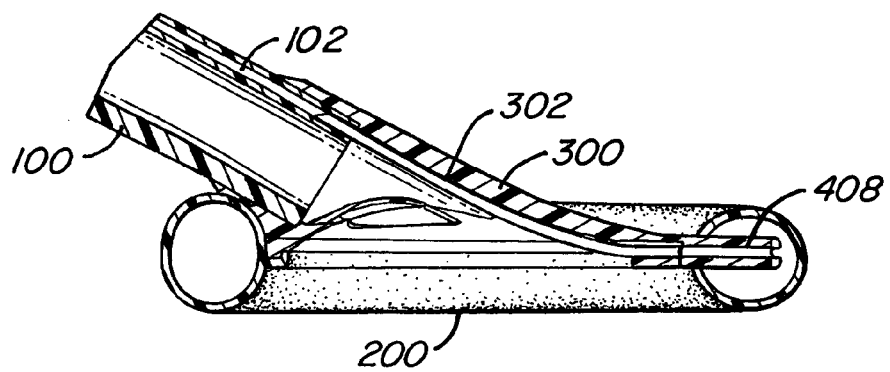
FIG. 7 is a detailed cross sectional view diagram of the distal end of a laryngeal airway device in accordance with an embodiment of the present invention.

FIG. 7 is a detailed cross sectional view diagram of the distal end of a laryngeal airway device in accordance with an embodiment of the present invention. FIG. 7 shows the tube 100 connected at its distal end with the dome 300. The tube has a passage 102 formed therein to receive the air inflation line 400. The air inflation line passes through passage 102 in the tube 100, continues in groove 302 in the dome 300 and ends at the protruding dome tip 408. Dome tip 408 fits inside the cuff 200 to provide a flow passage for inflating or deflating the cuff.

Figure 8:
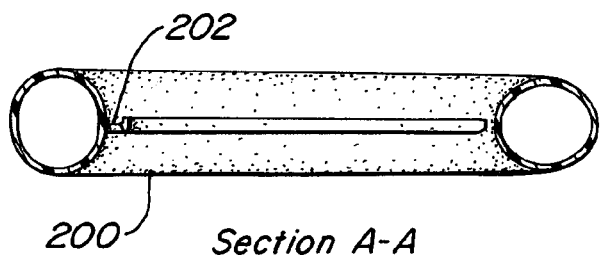
FIG. 8 is a detailed view diagram of the cuff of a laryngeal airway device in accordance with an embodiment of the present invention.
Figure 8:
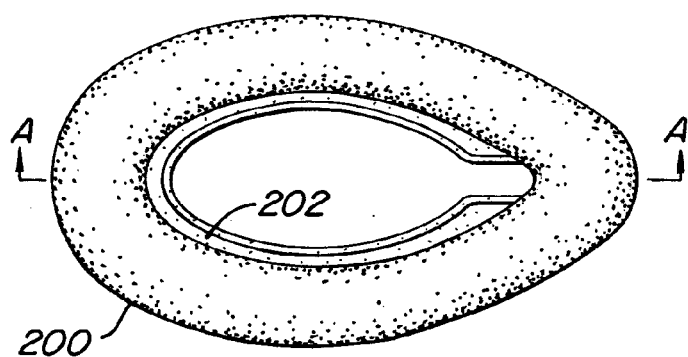
Figure 8:
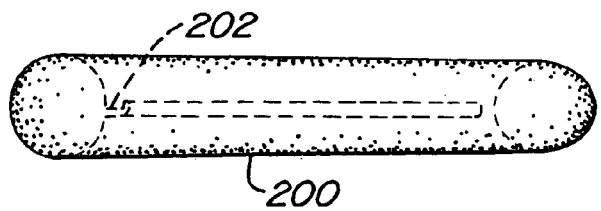

FIG. 8 is a detailed view diagram of the cuff 200 of a laryngeal airway device in accordance with an embodiment of the present invention. The cuff 200 includes a channel 202 on its inner surface that is configured to couple with a complimentarily shaped tray 412 (shown in FIG. 4) on the lower side of the dome 300. The cuff 200 is formed without any protrusions on the external surface of the cuff, as described above.

Figure 9:
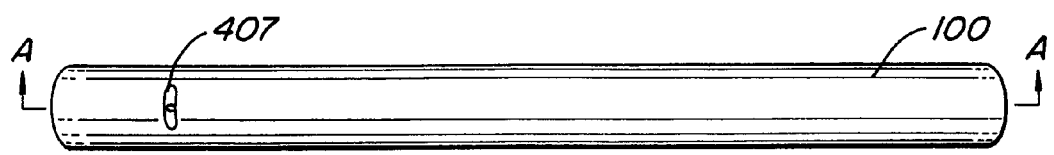
FIG. 9 is a diagram of an embodiment of the airway tube of the laryngeal airway device in accordance with an embodiment of the present invention.
Figure 9:
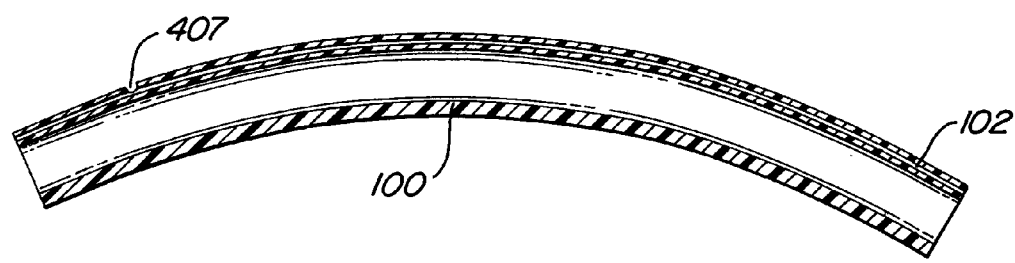

FIG. 9 is a diagram of an embodiment of the airway tube 100 of the laryngeal airway device in accordance with an embodiment of the present invention. FIG. 9 shows the airway tube 100 to include a passage 102 that is configured to receive the air inflation line 400 (shown in FIG. 2). Furthermore, FIG. 9 shows the inflation line insertion location 407 formed offset from the proximal end of the tube 100. An inflation line 400 (shown in FIG. 2) enters the tube 100 at the inflation line insertion location 407 and feeds through the tube 100 to connect with and inflate or deflate the cuff.

The improved device described herein is manufactured using medical grade plastic materials, such as for example a medical grade PVC. The novel features of the improved device described herein can all be combined into one laryngeal airway device, or alternately a suite of different laryngeal airway devices can be produced each having one or a combination of the novel features that have been described herein. It is also envisioned that various different size devices according to the embodiments of the present invention will be made available to accommodate different size patients, from neonates to adult patients.

As will be understood by those skilled in the art, the present invention may be embodied in other specific forms without departing from the essential characteristics thereof. For example, a device in accordance with the embodiments of the present invention can be made using various different materials and in many different sizes. These other embodiments are intended to be included within the scope of the present invention, which is set forth in the following claims.

What is claimed is:

1. A laryngeal airway device, comprising:
   an airway tube having a proximal end and a distal end;
   a dome having an inlet and an outlet, the inlet of the dome connected with the distal end of the airway tube;
   an inflatable cuff connected about a periphery of the outlet of the dome; and
   a cuff inflation line configured to be in fluid communication with an internal space of the cuff;
   wherein the outlet comprises an aperture and a plurality of protrusions extending only partially into the aperture, and wherein one of the protrusions is relatively flexible as compared to the remainder of the plurality of protrusions.

2. The device of claim 1 wherein the relatively flexible one of the plurality of protrusions comprises a flexible flap.

3. The device of claim 1 wherein the relatively flexible one of the plurality of protrusions is configured to push a patient's epiglottis in response to a device being inserted into the airway tube and through the aperture.

4. The device of claim 1 wherein the relatively flexible one of the plurality of protrusions is larger than the remainder of the plurality of protrusions.

5. The device of claim 1 wherein the protrusions are radially spaced about the outlet.

6. The device of claim 1 comprising a protruding dome tip at a distal end of the outlet of the dome, the protruding dome tip having a distal end being located in the internal space of the cuff.

7. The device of claim 6 wherein the cuff inflation line passes through the protruding dome tip.

8. The device of claim 1 wherein the outlet of the dome comprises a tray portion, and wherein the cuff comprises a channel on an inner surface of the cuff, the channel being connected with the periphery of the outlet of the dome at the tray portion.

9. The device of claim 1 wherein the cuff comprises a mold extraction orifice at its distal end formed on an inner surface of the cuff, and wherein the cuff inflation line is configured to be in fluid communication with the internal space of the cuff at an opening comprising the mold extraction orifice.

10. The device of claim 1 comprising a removable connector connected with the proximal end of the airway tube.

11. The device of claim 1 wherein the cuff inflation line is configured to be in fluid communication with the internal space of the cuff at a distal end of the cuff.

12. The device of claim 11 wherein at least a portion of the cuff inflation line comprises a passage formed along a portion of the airway tube opposite the outlet of the dome.

13. A laryngeal airway device, comprising:
an airway tube having a proximal end and a distal end;
a dome having an inlet and an outlet, the inlet of the dome connected with the distal end of the airway tube;
an inflatable cuff connected about a periphery of the outlet of the dome;
a cuff inflation line configured to be in fluid communication with an internal space of the cuff; and
a protruding dome tip at a distal end of the outlet of the dome, the cuff inflation line extending through the protruding dome tip.

14. The device of claim 13 wherein the protruding dome tip is less flexible than the cuff, so as to oppose the cuff from folding back on itself when the device is inserted into a patient.

15. The device of claim 13, wherein the cuff inflation line passes through the protruding dome tip.

16. The device of claim 15 wherein the protruding dome tip comprises a slit at its distal end, so as to cause the protruding dome tip to maintain fluid communication with the internal space of the cuff when the cuff is adjacent to the distal end of the protruding dome tip.

17. The device of claim 13, wherein the cuff inflation line reinforces the length of the dome.

18. A laryngeal airway device, comprising:
an airway tube having a proximal end and a distal end;
a dome having an inlet and an outlet, the inlet of the dome connected with the distal end of the airway tube;
an inflatable cuff connected about a periphery of the outlet of the dome; and
a cuff inflation line configured to be in fluid communication with an internal space of the cuff and having an outlet at a distal end of the cuff.

19. The device of claim 18 wherein a portion of the length of the cuff inflation line is placed in a passage formed in a wall of the airway tube.

20. A laryngeal airway device, comprising:
an airway tube having a proximal end and a distal end;
a dome having an inlet and an outlet comprising an aperture, the inlet of the dome connected with the distal end of the airway tube;
an inflatable cuff connected about a periphery of the outlet of the dome;
a cuff inflation line configured to be in fluid communication with an internal space of the cuff; and
no more than one flexible epiglottis barrier attached to the outlet of the dome, the flexible epiglottis barrier extending only partially into the aperture.

21. The device of claim 20, wherein the flexible epiglottis barrier functions as a human epiglottis during the ebb and flow of air through the device.

22. A laryngeal airway device comprising:
an airway tube having a proximal end and a distal end;
a dome having an inlet and an outlet, the dome connected at its inlet with the distal end of the airway tube;
an inflatable cuff connected with a periphery of the outlet of the dome, the cuff having a proximal end and a distal end; and
a cuff inflation line in fluid communication with the distal end of the cuff such that upon inflation, the cuff inflates from its distal end.

23. The device according to claim 22, wherein at least a portion of the inflation line is embedded in the dome.

24. The device according to claim 22, wherein the airway tube has a wall with inner and outer surfaces, and at least a portion of the inflation line runs along the tube between the inner and outer surfaces.

25. The device according to claim 24 wherein the dome comprises a front side and a back side, the front side including the dome outlet, the airway tube comprising a front side and a back side, the distal end of the back side of the tube being connected to the back side of the dome, said inflation line running along the back side of the tube.

26. The device according to claim 22, wherein the dome has a proximal end and a distal end, the dome further comprising a protrusion extending from its distal end into the cuff.

27. The device according to claim 26, wherein the protrusion is less elastic than the cuff.

28. The device according to claim 22, wherein the inflation line is in fluid communication with the protrusion.

29. The device according to claim 22, wherein the dome comprises a groove and wherein the cuff inflation lines runs in the groove.

30. The device according to claim 22, wherein the outlet of the dome comprises a tray portion, and the cuff comprises a channel on the inner surface of the cuff, the channel being connected with the periphery of the outlet of the dome at the tray portion.

31. The device according to claim 22, wherein the cuff comprises a mold extraction orifice at its distal end formed on an internal surface of the cuff, and wherein the cuff inflation line is configured to be in fluid communication with the internal space of the cuff at an opening comprising the mold extraction orifice.

32. The device according to claim 22, comprising a removable connector connected with said proximal end of the airway tube.

33. The device according to claim 22, comprising an inflation line insertion point offset distally from the proximal end of the airway tube.

34. A laryngeal airway device, comprising:
an airway tube having a proximal end and a distal end;
a dome having an inlet and an outlet, the outlet having a proximal end and a distal end, the dome connected at its inlet with the distal end of said airway tube;
an inflatable cuff having a proximal end and a distal end, an inside and an outside, and connected with the periphery of the outlet of the dome;
a cuff inflation line having a proximal end and a distal end; and
a protruding dome tip extending from the distal end of the dome outlet into the inside of the distal end of the cuff, the tip in fluid communication with the distal end of the inflation line and the inside of the cuff.

35. The device according to claim 34, wherein the protruding dome tip is less elastic than said cuff.

36. The device according to claim 34, wherein the airway tube has a wall with inner and outer surfaces, and at least a portion of the cuff inflation line is located between the inner and outer surfaces.

37. A laryngeal airway device, comprising:
an airway tube having a proximal end and a distal end, the tube having a wall comprising inner and outer surfaces, the tube having a front side and a back side;
a dome having an inlet and an outlet and a front side and a back side, the outlet located on the front side, the dome connected at its inlet with the distal end of said airway tube wherein the back side of the dome connects with the back side of the distal end of the tube, the dome defining an aperture between the inlet and the outlet and having at least one protrusion extending from the dome into the aperture;

an inflatable cuff having an inside and an outside and a proximal end and a distal end, the cuff connected with a periphery of the outlet of said dome;

a cuff inflation line having a proximal end and a distal end, the cuff inflation line in fluid communication with the inside of said cuff, wherein at least a portion of the line runs from the dome inlet to the dome outlet.

38. The device according to claim 37, wherein the at least one protrusion is of insufficient length to contact the dome on both sides of the aperture.

39. A laryngeal airway device, comprising:

an airway tube having a proximal end and a distal end, the airway tube having an internal passage in a wall of the airway tube;

a dome having an inlet and an outlet and a proximal end and a distal end, the dome connected at its inlet with said distal end of said airway tube, the dome defining an aperture between the inlet and the outlet, the dome including no more than one flexible non-hinged protrusion partially extending into said aperture from the proximal end of said dome;

an inflatable cuff having an inside and an outside connected with a periphery of the outlet of the dome, the cuff having a distal end and a proximal end; and a cuff inflation line having a proximal end and a distal end, wherein the distal end of the cuff inflation line is in fluid communication with the inside of the cuff such that upon inflation, the cuff is inflated from its distal end.

40. The device according to claim 39, wherein the protrusion is of insufficient length to contact the dome on both sides of the aperture.

41. The device according to claim 39, wherein the protrusion extends from the distal end of the dome into the inside of the cuff.

42. The device according to claim 39, wherein the protrusion is less elastic than the cuff.

43. The device according to claim 39, wherein the protrusion includes a passage therein in fluid communication with the cuff inflation line and the inside of the cuff.

* * * * *